United States Patent
Yee

(10) Patent No.: US 8,182,471 B2
(45) Date of Patent: May 22, 2012

(54) INTRASTROMAL REFRACTIVE CORRECTION SYSTEMS AND METHODS

(75) Inventor: Kingman Yee, San Jose, CA (US)

(73) Assignee: AMO Manufacturing USA, LLC., Santa Ana, CA (US)

( * ) Notice: Subject to any disclaimer, the term of this patent is extended or adjusted under 35 U.S.C. 154(b) by 1492 days.

(21) Appl. No.: 11/677,504

(22) Filed: Feb. 21, 2007

(65) Prior Publication Data

US 2007/0219543 A1    Sep. 20, 2007

Related U.S. Application Data

(60) Provisional application No. 60/783,306, filed on Mar. 17, 2006.

(51) Int. Cl.
    *A61B 18/18* (2006.01)
(52) U.S. Cl. ............................... 606/5; 606/4
(58) Field of Classification Search .................. 606/4–6, 606/107, 166
    See application file for complete search history.

(56) References Cited

U.S. PATENT DOCUMENTS

| | | |
|---|---|---|
| 4,764,930 A | 8/1988 | Bille et al. |
| 4,848,340 A | 7/1989 | Bille et al. |
| 4,881,808 A | 11/1989 | Bille et al. |
| 4,901,718 A | 2/1990 | Bille et al. |
| 4,907,586 A | 3/1990 | Bille et al. |
| 4,988,348 A | 1/1991 | Bille |
| 5,221,988 A | 6/1993 | Juhasz |
| 5,246,435 A | 9/1993 | Bille et al. |
| 5,336,215 A | 8/1994 | Hsueh et al. |
| 5,439,462 A | 8/1995 | Bille et al. |
| 5,541,951 A | 7/1996 | Juhasz et al. |
| 5,548,234 A | 8/1996 | Turi et al. |
| 5,549,632 A * | 8/1996 | Lai ...................................... 606/5 |
| 5,561,678 A | 10/1996 | Juhasz et al. |
| 5,882,338 A * | 3/1999 | Gray ............................. 604/131 |
| 5,984,916 A | 11/1999 | Lai |
| 5,993,438 A | 11/1999 | Juhasz et al. |
| 6,004,313 A | 12/1999 | Shimmick et al. |
| 6,110,166 A | 8/2000 | Juhasz |
| 6,143,011 A * | 11/2000 | Hood et al. .................... 606/166 |
| 6,146,405 A | 11/2000 | Johnston |
| 6,254,595 B1 | 7/2001 | Juhasz et al. |
| 6,324,191 B1 | 11/2001 | Horvath |
| 6,325,792 B1 * | 12/2001 | Swinger et al. .................... 606/4 |
| 6,342,053 B1 * | 1/2002 | Berry ................................. 606/5 |
| 6,344,040 B1 | 2/2002 | Juhasz et al. |
| 6,373,571 B1 | 4/2002 | Juhasz et al. |
| 6,520,956 B1 | 2/2003 | Huang |
| 6,551,306 B1 * | 4/2003 | Carriazo ............................ 606/5 |

(Continued)

FOREIGN PATENT DOCUMENTS

DE    103 54 025 A1    6/2005

(Continued)

*Primary Examiner* — Sam Yao
*Assistant Examiner* — Lynsey Crandall
(74) *Attorney, Agent, or Firm* — AMO Manufacturing USA, LLC

(57) ABSTRACT

Devices, systems, and methods for laser eye surgery selectively ablate tissues within the cornea of an eye along one or more target surfaces, so that corneal tissue bordered by the laser incision surface(s) can be mechanically removed. An appropriate tissue-shaping surface can be selected based on the regular refractive error of the eye, and a shape of the target laser surface(s) can be calculated so as to correct irregular refractive errors of the eye, impose desired additional spherocylindrical and/or irregular alterations.

31 Claims, 10 Drawing Sheets

U.S. PATENT DOCUMENTS

| | | | |
|---|---|---|---|
| 6,623,476 B2 | 9/2003 | Juhasz et al. | |
| 6,648,877 B1 | 11/2003 | Juhasz et al. | |
| 6,676,653 B2 | 1/2004 | Juhasz et al. | |
| 6,685,319 B2 * | 2/2004 | Watson et al. | 351/219 |
| 6,730,074 B2 * | 5/2004 | Bille et al. | 606/5 |
| 6,751,033 B2 | 6/2004 | Goldstein et al. | |
| 6,863,667 B2 | 3/2005 | Webb et al. | |
| 6,899,707 B2 | 5/2005 | Scholler et al. | |
| 6,902,561 B2 | 6/2005 | Kurtz et al. | |
| 6,942,656 B2 * | 9/2005 | Pawlowski et al. | 606/4 |
| 6,991,629 B1 | 1/2006 | Juhasz et al. | |
| 6,992,765 B2 | 1/2006 | Horvath et al. | |
| 7,018,376 B2 | 3/2006 | Webb et al. | |
| 7,027,233 B2 | 4/2006 | Goldstein et al. | |
| 7,044,602 B2 | 5/2006 | Chernyak | |
| 7,189,224 B2 | 3/2007 | Kurtz et al. | |
| 7,780,653 B2 * | 8/2010 | Hovanesian | 606/4 |
| 7,922,735 B2 * | 4/2011 | Daxer | 606/166 |
| 2003/0004500 A1 | 1/2003 | Clapham et al. | |
| 2003/0223037 A1 * | 12/2003 | Chernyak | 351/209 |
| 2004/0169820 A1 | 9/2004 | Dai et al. | |
| 2004/0225284 A1 | 11/2004 | Webb et al. | |
| 2004/0243112 A1 | 12/2004 | Bendett et al. | |
| 2005/0192562 A1 | 9/2005 | Loesel et al. | |
| 2006/0084954 A1 | 4/2006 | Zadoyan et al. | |
| 2006/0114469 A1 | 6/2006 | Horvath et al. | |
| 2006/0155265 A1 | 7/2006 | Juhasz et al. | |
| 2006/0195078 A1 | 8/2006 | Webb et al. | |
| 2006/0264917 A1 * | 11/2006 | Tuan et al. | 606/5 |
| 2007/0093796 A1 | 4/2007 | Raksi et al. | |
| 2007/0106285 A1 | 5/2007 | Raksi | |
| 2007/0173791 A1 | 7/2007 | Raksi | |
| 2008/0228176 A1 * | 9/2008 | Triebel et al. | 606/4 |
| 2008/0234707 A1 * | 9/2008 | Muehlhoff et al. | 606/166 |
| 2009/0234335 A1 * | 9/2009 | Yee | 606/5 |

FOREIGN PATENT DOCUMENTS

| | | |
|---|---|---|
| EP | 1 364 632 A1 | 11/2003 |
| WO | WO 94/09849 A1 | 5/1994 |
| WO | WO 2005/039462 A1 | 5/2005 |
| WO | WO 2007/109399 A1 | 9/2007 |
| WO | WO9808048 A1 | 10/2007 |

* cited by examiner

INTRASTROMAL REFRACTIVE CORRECTION SYSTEMS AND METHODS

CROSS-REFERENCES TO RELATED APPLICATIONS

This application is a nonprovisional application claims the benefit of U.S. provisional patent application No. 60/783,306, filed on Mar. 17, 2006, the disclosure of which is incorporated herein by reference.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

This invention generally relates to laser eye surgery devices, systems, and methods. In particular embodiments, the invention provides techniques for selectively altering refractive properties of corneas having regular and/or irregular optical defects, often by directing energy into the stroma.

Laser eye surgery systems and methods are now used to correct defects in vision, often using a technique known as ablative photodecomposition. In general, this technique applies a pattern of laser radiation to an exposed corneal tissue so as to selectively remove and resculpt the cornea. The pattern of laser energy often includes a series of discrete laser pulses from an excimer laser, with the locations, sizes, and/or numbers of pulses of the pattern being calculated to achieve a desired volumetric resculpting of the cornea, and to thereby create enhanced optical properties or treat optical defects.

Many patients suffer from optical defects which are not easily treated using standard glasses and contact lenses. Glasses and contacts often treat only regular or spherical and cylindrical refractive errors of the eye. Wavefront diagnostic techniques have been developed to measure irregular refractive errors, and these techniques have proven highly useful in determining customized refractive prescriptions for these patients. The flexibility of laser photorefractive decomposition offers hope to these patients, as this technique can be used to resculpt the eyes to correct both regular and irregular refractive errors. By combining laser eye surgery techniques with wavefront diagnostic approaches, it is often possible to achieve visual acuity measurements of 20/20 or better for many patients.

Early laser eye surgery treatments often involved the removal of the epithelial layer before changing the shape of the underlying corneal tissue. The epithelial layer tends to regrow, whereas volumetric resculpting of the underlying stroma can provide long-lasting effects. Corneal resculpting techniques involving mechanical abrasion or laser ablation of the epithelial layer so as to expose the underlying stroma for volumetric photoablative decomposition are often referred to as photorefractive keratectomy ("PRK"), and PRK remains a good option for many patients. In the last several years, alternative techniques involving formation of a flap of corneal tissue (including the epithelial layer) have gained in popularity. Such techniques are sometimes popularly referred to "flap-and-zap," or laser in situ keratomileusis ("LASIK"). LASIK and related variations often have the advantage that vision can be improved within a few hours (or even minutes) after surgery is complete. LASIK flaps are often formed using mechanical cutting blades or microkeratomes, and the flap of epithelial tissue can be temporarily displaced during laser ablation of the stroma. The flap can reattach to the underlying stroma quite quickly, and the patient need not wait for epithelial tissue regrowth to experience the benefits of laser resculpting, so that these procedures are safe and highly effective for many patients.

A variety of alternative refraction altering techniques have also been proposed. In particular, focusing of femtosecond laser energy within the stroma so as to ablate a volume of intrastromal tissue has been proposed. By scanning the focal spot within an appropriate volume of the stromal tissue, it might be possible to vaporize the volume so as to achieve a desired refractive alteration. Despite possible advantages of intrastromal volumetric ablation techniques, these approaches have not yet gained the popularity of LASIK and/or PRK. Intrastromal femtosecond ablation techniques have, however, begun to gain popularity as a method for incising the cornea so as to form the flap of corneal tissue in LASIK and related procedures. Unfortunately, this combined approach often involves the use of both a fairly expensive intrastromal femtosecond laser for incising the corneal tissues, and then an excimer laser for resculpting the exposed stroma. The combined use these two separate, fairly complex and/or expensive laser systems may limit the acceptability and benefits of these new refractive laser eye surgery techniques.

In light of the above, it would generally be desirable to provide improved devices, system, and methods for laser eye surgery. It would be particularly desirable to expand the capabilities of lasers and allow their use for both incising and refractively altering the eye. It would be particularly desirable if such improved devices were suitable for correction of regular refractive errors and a irregular refractive alterations (such as correcting an irregular refractive error of the eye), ideally without having to resort to two separate laser systems.

BRIEF SUMMARY OF THE INVENTION

The present invention generally provides improved devices, systems, and methods for laser eye surgery. In many embodiments, the invention will make use of femtosecond (or optionally picosecond) lasers and their ability to selectively ablate tissues within the cornea of an eye. By focusing energy from these lasers at a focal spot within a corneal stroma, and by scanning the spot along a surface, such lasers can quickly and accurately incise the corneal tissues along that surface. Rather than attempting to rely on volumetric intrastromal tissue vaporization, embodiments of the invention may largely (or even primarily) employ mechanical removal of tissues bordered by a laser incision surface. Advantageously, large variations in depth of the focal spot from a plane (or other surface, such as a sphere or the like) may be avoided by pre-shaping the corneal tissues using a tissue-shaping surface. By selecting an appropriate tissue-shaping surface based on the regular refractive error of the eye, and by calculating an appropriate tissue incision surface so as to correct irregular refractive errors of the eye, the corneal reshaping may mitigate both regular and irregular refractive defects, with the laser treatment typically being completed in less than 100 seconds, often being completed in less than 50 seconds, in many cases being completed in less than 30 seconds, and in some cases being completed in less than 10 seconds between initiation of and completion of the laser ablation.

In a first aspect, the invention provides a method for altering refraction of an eye. The eye has a regular refractive error and is capable of benefiting from a desired irregular refractive alteration. The method comprises selecting a tissue-shaping surface substantially corresponding to the regular refractive error. The selected tissue shaping surface is engaged against the eye so as to conform the eye to the selected tissue-shaping surface. A laser target surface is determined in response to the desired irregular refractive alteration of the eye. A laser spot is scanned through the tissue of the eye along the laser target surface so as to mitigate the regular error and effect the desired irregular refractive alteration of the eye.

In many embodiments, the desired irregular refractive alteration of the eye will comprise correction of irregular refractive defects, typically based on wavefront measurements of the eye. Other desirable irregular refractive alterations may include imposing a presbyopia-mitigating refractive shape on the eye. Such irregular refractive alterations will often be customized for a particular patient, optionally being based on pupil measurements taken from the eye under different viewing conditions and the like.

An appropriate tissue-shaping surface will often be selected by choosing a shaping body from among a set of alternative shaping bodies. The shaping bodies will each have tissue-shaping surfaces that correspond to an associated regular refractive error. For example, one subset of the bodies may be used for patients having about 2.0 D of myopia, with members of this subset each having an associated astigmatism power (for example, −2.0 D, 0 D, +2 D, 4 D . . . of cylinder). Another subset of the bodies may have surface with 4 D of myopia (and differing amounts of astigmatism), and so on. The steps in spherical and cylindrical power between the various shaping bodies of the set may be uniform (such as having steps of 0.5 D, steps of 1.0 D, steps of 1.5 D, or the like) or the incremental step size may vary throughout the set. Regardless, the actual regular error of the eye will often differ at least slightly from the power of the selected shaping body. Advantageously, the laser target surface may be calculated so as to compensate for this power difference. Hence, when a patient has 2.3 D of myopia, and the substantially corresponding tissue-shaping surface has 2.0 D of spherical power, the laser target surface may be adjusted so as to provide an additional 0.3 D of spherical power to fully correct the patient's myopia. Typically, the steps in power between the tissue-shaping surfaces of the set will each be less than or equal to two times a maximum power adjustment available from the laser target surface. In exemplary embodiments, the steps in power may be less than or equal to 3.0 D, often being less than or equal to 1.5 D, and in some embodiments being less than or equal 0.75 D.

In exemplary embodiments, each of the set of shaping bodies may comprises a material transmissive of the laser energy used to form the spot. Each shaping body may have alignment surfaces for aligning body both along an optical path of the laser energy and rotationally about the optical path. The bodies may each also have a signal source configured to generate a signal indicative of an associated power of that body, and of an identifier of that particular body. This may allow the signals to be used for verifying that an appropriate body has been mounted to the laser eye surgery system, and for inhibiting reuse of each of the alternative selectable bodies. Suitable signal sources may comprise a memory chip, a radio frequency identification ("RFID") tag, or the like.

In many cases, the regular error of the eye will comprise a cylindrical error having an astigmatism axis. The tissue-shaping surface will often be rotated into alignment with the astigmatism axis of the eye. Alignment between the tissue-shaping surface and the eye may be checked after engaging the tissue-shaping surface against the eye, such as by capturing an image of the eye through the tissue shaping surface so as to determine horizontal and/or cyclotorsional offsets between the engaged eye and the tissue-shaping surface. Optionally, the tissue-shaping surface may be displaced away from the eye, and either the eye or the tissue-shaping surface moved so as to correct alignment before again engaging the tissue-shaping surface against the eye. While such repositioning may be appropriate when the offsets exceed a threshold, some limited alignment offsets may be acceptable. The range of acceptable offsets may be increased by adjusting a location and/or a shape of the target laser surface in response to any alignment offsets.

In many embodiments, tissue will be at least partially mechanically excised from between the target laser surface and the tissue-shaping surface. By removing substantially all of the tissue between the target tissue surface and the tissue-shaping surface (often after separation of the tissue-shaping surface from the eye) both regular and irregular refractive errors of the eye can be corrected, with the benefits of the correction often being provided after epithelial regrowth. In other embodiments, the laser spot may be scanned along another laser target surface so that first and second tissue surfaces are defined by the two laser target surfaces. Tissue may be mechanically excised from between these two laser-formed tissue surfaces so that the eye has enhanced refractive characteristics when the two tissue surfaces engage each other, and without having to wait for epithelial regrowth.

In another aspect, the invention provides a method for customized correction of an eye. The method comprises measuring a regular refractive error and an irregular refractive error of the eye. The regular refractive error comprises a spherical error and a cylindrical error. The cylindrical error has a cylindrical power and an astigmatism axis. A tissue-shaping body is selected in response to the regular refractive error of the eye. The tissue-shaping body is selected from among a set of alternative tissue-shaping bodies having differing associated spherical and cylindrical powers. The selected tissue-shaping body has a selected tissue-shaping surface with a spherical power substantially corresponding to the spherical power of the eye and a cylindrical power substantially corresponding to the cylindrical error of the eye. A cylindrical axis of the selected tissue-shaping body is aligned with the astigmatism axis of the eye, and the selected tissue-shaping surface is engaged against the eye so as to conform an eye surface to the selected tissue-shaping surface. A target laser surface is determined in response to the irregular refractive error of the eye, and tissue of the eye is incised by scanning a laser spot through the tissue along the laser target surface. Tissue bordered by the laser target surface is mechanically excised so as to mitigate the regular refractive error and the irregular refractive error of the eye.

In many embodiments, the target laser surface differs from a nominal surface shape (such as a plane or a sphere) by less than a depth threshold, the depth threshold corresponding to a power of about 1.5 diopters or less.

In another aspect, the invention provides a system for altering refraction of an eye. The eye has a regular refractive error and is capable of benefiting from an irregular refractive alteration. The system comprises a set of alternative tissue-shaping bodies having tissue-shaping surfaces and differing regular refractive powers. A tissue incising laser transmits a laser beam along an optical path, and a support positions a selected tissue-shaping body along the optical path. The selected tissue-shaping body is selected from among the set. A processor determines a laser target surface in response to the desired irregular refractive alteration of the eye. Beam scanning optics scan the beam along the laser target surface to incise tissue of the eye when the eye engages and conforms to the selected tissue-shaping surface such that removal of the incised tissue mitigates the regular error of the eye and effects the desired irregular alteration.

In another aspect, the invention provides a tissue-shaping body for use with a system to alter refraction of an eye. The eye will often have a regular refractive error and an irregular refractive error, the system including a support for positioning the shaping body along an optical path from a laser and beam scanning optics for scanning along a target surface to incise tissue of the eye when the eye engages the body such that removal along the incised tissue surface mitigates the regular and irregular errors of the eye. The body comprises a material transmissive of light from the laser, and a tissue shaping surface defined by the material. The tissue-shaping surface has a cylindrical power substantially corresponding to the regular refractive error of the eye.

In many embodiments, the body will also include a signal source for transmitting a signal. The signal will typically be indicative of the cylindrical power, and of an identifier of the particular body, the identifier typically comprising a serial number, an inventory number, or the like suitable for inhibiting reuse of that body. The body may be included in a set of alternatively selectable tissue-shaping bodies having differing tissue-shaping surfaces corresponding to differing cylindrical and spherical refractive powers. Each body will often have mounting interface surfaces for mounting the body relative to the laser system, with the mating interface surfaces generally positioning the tissue-shaping surface axially along an optical path of the laser and rotationally about the optical path so as to facilitate alignment of the cylindrical power of the body with an astigmatism axis of the eye. The body may also have (or be associated with) indicia of alignment to facilitate aligning the tissue-shaping surface and eye, for measuring horizontal and rotational offsets between the tissue-shaping surface and the eye, and/or he like.

DETAILED DESCRIPTION OF THE SPECIFIC EMBODIMENTS

Figure 1:
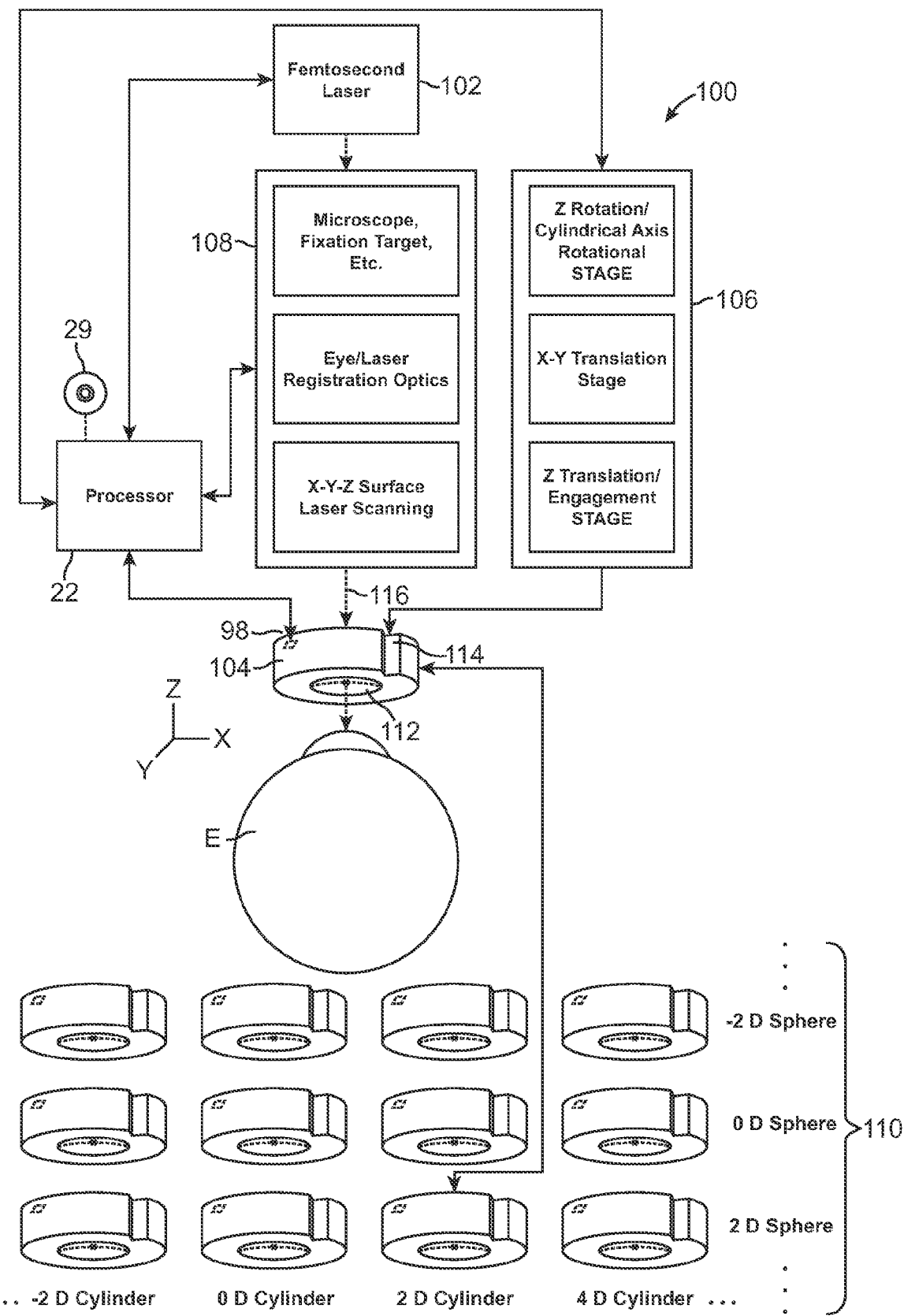
FIG. 1 schematically illustrates an exemplary laser eye surgery system and method of its use for correcting regular and irregular refractive errors of an eye.

The present invention generally provides improved devices, systems, and methods for refractive correction of an eye. Embodiments of the invention can take advantage of the capabilities of femtosecond lasers, picosecond lasers and the like, to incise the eye along precisely defined target surfaces. Advantageously, the volume of each individual laser ablation need not be precisely known and/or controlled, particularly when the total volume of tissue removal will be much greater than the overall volumetric ablation. Even when the absolute depth of individual ablations is not perfectly controlled or known, focused intrastromal laser ablations may be able to incise the corneal tissue along a surface shape with sufficient accuracy (such as by controlling the depths of ablation spots along a target surface relative to each other) so as to provide a desired high order resculpting of the overall cornea. By relying at least in part on incising and mechanical removal of tissues along the incised tissue surfaces (rather than solely or even primarily on volumetric photoablation), precise corrections may be provided very rapidly.

Many embodiments of the invention will make use of a selected corneal tissue-shaping surface, with the surface often being selected in response to a low-order, regular refractive error of the eye. By pre-shaping the tissue of the eye using a tissue-shaping surface that substantially corresponds to the regular refractive error of the eye, and by calculating a three-dimensional laser target surface based on irregular refractive errors of the eye, any residual regular errors of the eye (such as differences between the selected tissue-shaping surface power and the measured refractive error of the eye), any aspherical presbyopia-mitigating shapes, and/or the like, the total variation in depth of the target laser surface can be limited to a relatively narrow range, even when correcting eyes having quite significant standard refractive errors. As the irregular errors, residual errors, and presbyopia-mitigating shapes may all be encompassed by surfaces that are close to a plane (or other convenient surface) once the eye conforms to the tissue-shaping surface, such an arrangement may allow intrastromal laser ablations to correct a wide range of patient refractive errors despite any limitations in the range of intrastromal focusing and ablation depth variability.

Exemplary embodiments of the invention include sets of tissue-shaping bodies, with each body of the set corresponding to a standard refractive error or error range. Each body will typically have at least one associated tissue-shaping surface with an associated spherical power and an associated cylindrical power. By selecting an appropriate body having spherical and/or cylindrical powers which substantially correspond to those of the eye, and by conforming the tissue of the eye to the tissue shaping surface of that body, the capabilities of intrastromal laser ablations for correction of a wide range of regular and irregular refractive defects may be significantly enhanced.

Referring now to FIG. 1, an exemplary system 100 is suitable for correcting regular and irregular refractive errors of eye E. System 100 generally directs laser energy from a femtosecond laser 102 to corneal tissues of eye E while those tissues are shaped by a selected shaping body 104. Shaping body 104 is supported and positioned by an electromechanical support structure 106, with the exemplary support structure having a series of motion stages for selectively positioning the body relative to the tissues of eye E. Optics 108 of system 100 selectively direct the laser energy from laser 102 into the corneal tissues, with the optics and support structure generally being under the control of a system processor or computer 22.

Shaping body 104 is selected from among a set of alternative shaping bodies 110. As schematically illustrated in FIG. 1, the shaping bodies of set 110 will often have a variety of differing spherical and/or cylindrical powers. The cylindrical and/or power differences (sometimes referred to as power steps or increments) between shaping bodies of set 110 may be related to the range of depths of a target laser surface that will be determined by processor 22 and implemented by laser 102 and optics 108. For example, if system 100 has sufficient intrastromal ablation depth variability to form target laser surfaces that provide spherical adjustments to eye E of up to 1.0 D in spherical power, the set of shaping bodies 110 may (if no other adjustments were desired) have incremental power steps of 2 D of spherical power or less. Such a set of shaping bodies, might, for example, include shaping bodies having −2.0 D, 0 D, 2.0 D, 4 D . . . of spherical correction. A patient having 2.2 D of spherical error could then be treated by using a 2 D spherical shaping body, and by adding an additional 0.2 D of spherical correction by appropriate shaping of the target laser surface used during the scanning of the laser energy. A patient with 1.7 D of spherical error might be treated with the same 2.0 D shaping body, but with 0.3 D of correction being removed via an appropriate target laser surface implemented using optics 108 under the direction of processor 22.

It will often be advantageous to maintain some range in depth of the laser scanning optics for correction of irregular stigmatism, imposition of presbyopia-mitigating shapes, and the like. As the range of intrastromal ablation depth may be less than 3.0 D of correction with some systems, the steps in power within set 110 will often be less than 6.0 D. The range in power that can be effected by intrastromal ablation of a surface may be less than 1.0 D in many embodiments, so that the power steps within set 110 will often be 2.0 D or less. Exemplary systems may allow laser surface adjustments of 0.75 D or less, so that the steps between spherical and/or cylindrical powers of set 110 may be 1.5 D or less, optionally being 1.0 D or less so as to provide sufficient irregular error treatment, presbyopia mitigation, and the like.

Shaping body 104 generally includes a distal tissue-shaping surface 112, with the tissue-shaping surface having a sphero-cylindrical shape corresponding to the associated nominal refractive correction of that body. Where the target laser surface will, for example, be nominally planar (with adjustments from the plane for irregular errors, residual powers, aspherical presbyopia-mitigation shapes, and/or the like), the tissue-shaping surface may directly have the curvature associated with its nominal power in corneal tissue. Where the target laser surface has a nominal spherical shape, the tissue-shaping surface may differ from that nominal spherical shape per the body nominal power, and so on. In the exemplary embodiment, a cylindrical side surface extends from the distal end of the body adjacent surface 112 to a flat (or optionally lens-shaped) proximal surface. The material along surface 112 (and typically from surface 112 to the proximal surface) comprises a material which is sufficiently transmissive of the laser energy from laser 102 to allow treatment eye E without overheating of the body, the tissue-shaping surface, and the engaged corneal tissues. Suitable materials may comprise, for example, glass, a suitable polymer such as PMMA, or the like. Body 104 will generally include positioning surfaces 114 that can be engaged by corresponding surfaces of the support structure 106 so as to accurately position the body horizontally (along the X-Y plane) relative to an optical axis 116 of the laser treatment (such as the cylindrical side surface, circular end walls and edges, or the like), and also so as to rotationally position the body 104 about the axis 116 (such as the notch illustrated). This will help facilitate rotational alignment of any cylindrical power of tissue-shaping surface 112 relative to the cylindrical astigmatism axis of eye E. A wide variety of alternative shaping bodies might also be implemented.

Figure 1A:
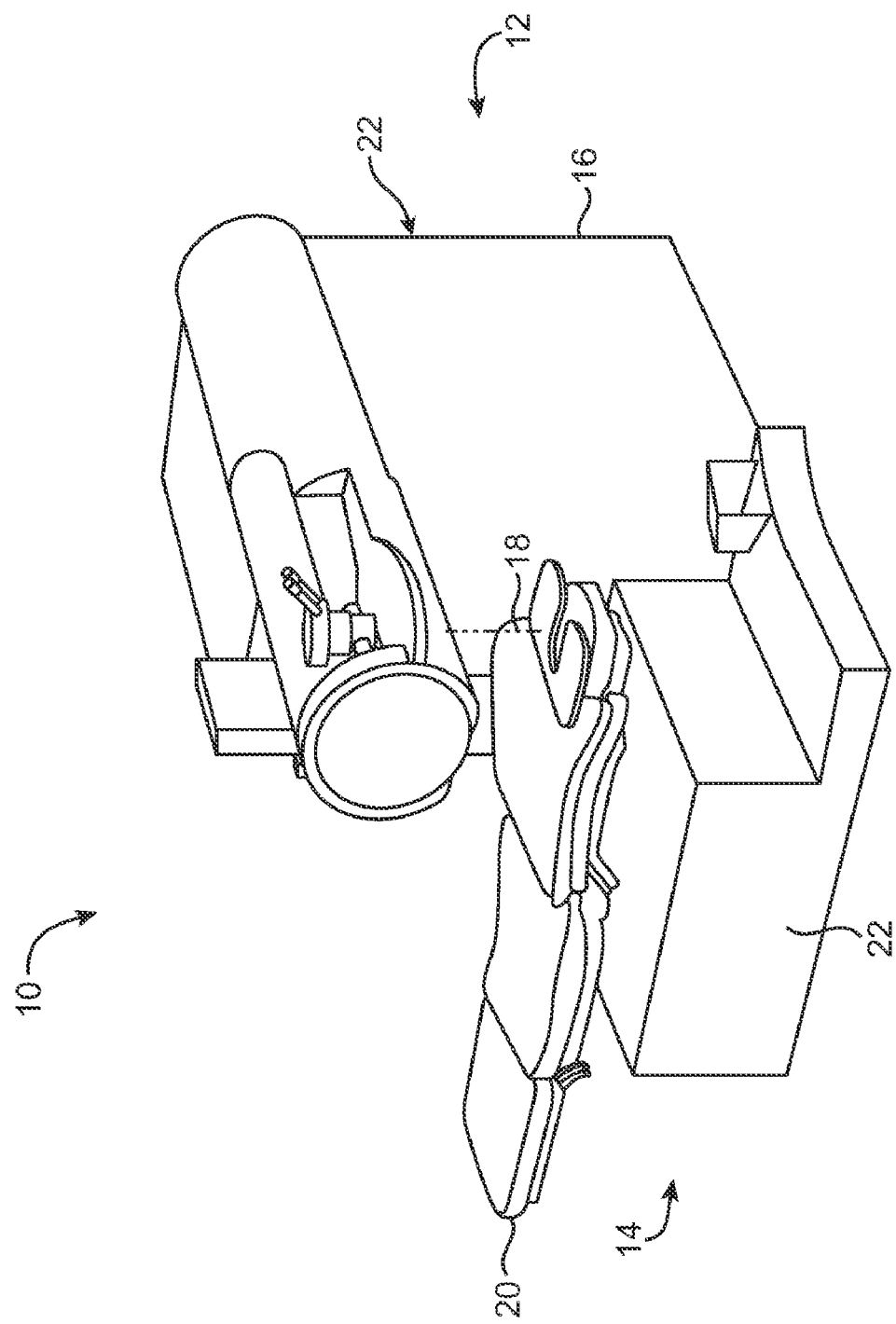
FIG. 1A is a schematic perspective view of a laser-eye surgery system and patient support system, components of which may be modified for use in the system of FIG. 1.

Referring now to FIGS. 1 and 1A, elements of system 100 may be incorporated into, and/or may make use of components of a laser eye surgery system 10. Laser eye surgery system 10 generally includes a laser system 12 and a patient support system 14. Laser system 12 includes a housing that contains both a laser and a system processor 22. The laser generates the laser beam 18, which is directed to a patient's eye under the direction of a system operator. Delivery optics used to direct the laser beam, the microscope mounted to the delivery optics, and the like may employ existing structures from commercially available laser systems, including at least some portions of the excimer refractive laser systems available from ADVANCED MEDICAL OPTICS, INC. of Santa Clara, Calif.

In addition to (or in some cases, instead of) adjustment to the delivery optics directing laser beam 18, alignment between the patient and the laser treatment system may be provided at least in part by the patient support system 14. Patient support system 14 generally includes a patient support 20 having an associated patient support movement mechanism. Patient support 20 may be contoured, helping to position the patient at a nominal location on the patient support. Large and fine adjustments of the patient support and patient may be effected using large and fine motion control mechanisms such as those more fully described in U.S. patent application Ser. No. 10/226,867 filed on Aug. 20, 2002, the disclosure of which is incorporated herein by reference.

Figure 2:
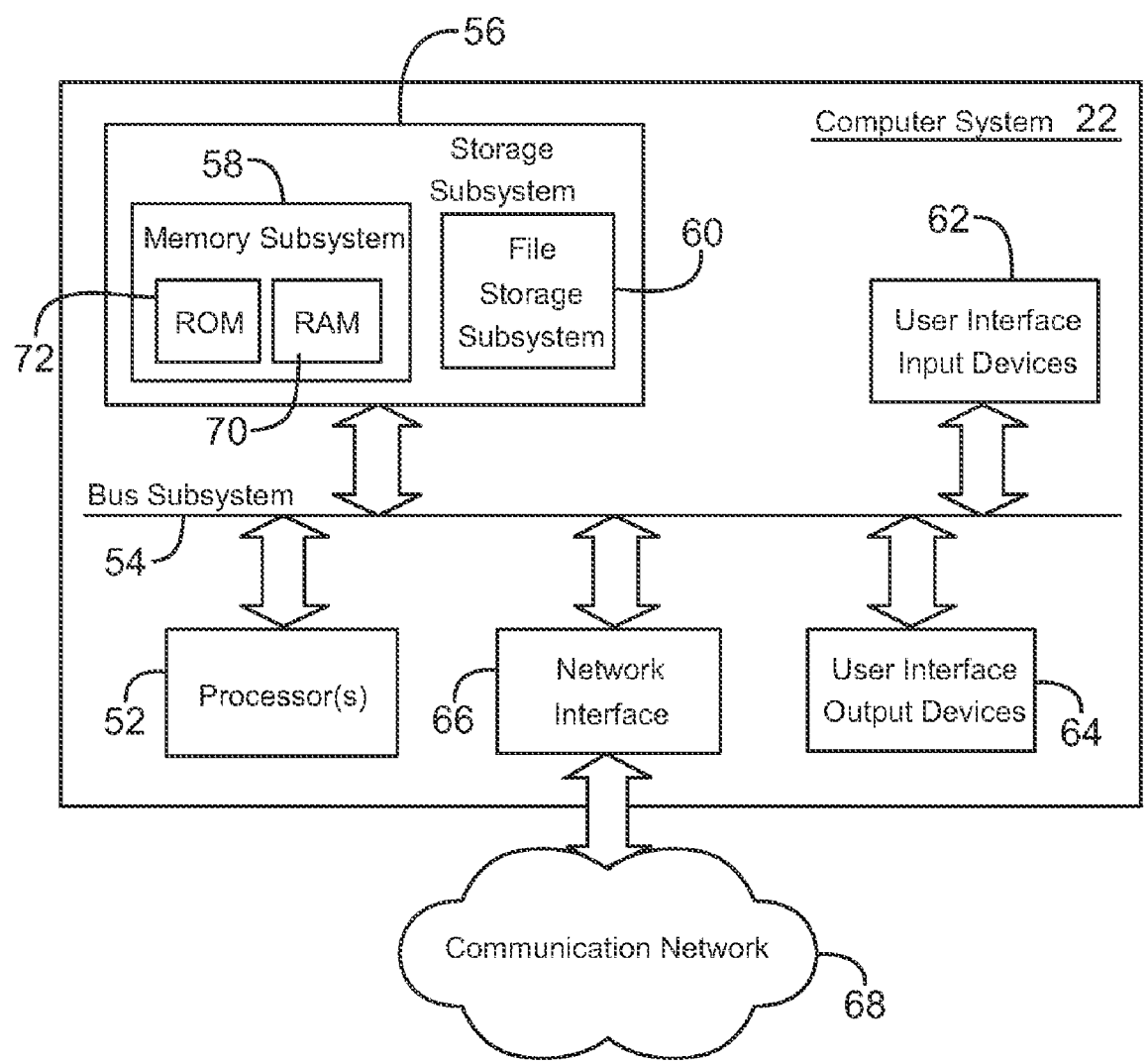
FIG. 2 is a schematic illustration of a data processing computer system for use in the laser eye surgery systems of FIGS. 1 and 1A.

FIG. 2 is a simplified block diagram of an exemplary computer system 22 that may be used by the laser surgical system 100. Computer system 22 typically includes at least one processor 52 which may communicate with a number of peripheral devices (and/or other processors) via a bus subsystem 54. These peripheral devices may include a storage subsystem 56, typically including a memory 58 and a file storage subsystem 60. The peripheral devices may also include one or more user interface input device 62, user interface output device 64, and a network interface subsystem 66. Network interface subsystem 66 can provide an interface to outside networks 68 and/or other devices, such as the wavefront measurement system 30 described below with reference to FIG. 3.

User interface input devices 62 may include a keyboard, pointing devices such as a mouse, trackball, touch pad, or graphics tablet, a scanner, foot pedals, a joystick, a touch screen incorporated into the display, audio input devices such as voice recognition systems, microphones, and other types of input devices. User input devices 62 will often be used to download a computer executable code from a tangible storage media 29 embodying any of the methods described herein. User output devices 64 may include a display subsystem, a printer, a fax machine, or non-visual displays such as audio output devices. The display subsystem may comprise a cathode ray tube (CRT), a flat-panel display such as a liquid crystal display (LCD), a projection device, or the like. The display subsystem may also provide a non-visual display such as via audio output devices. Storage subsystem 56 stores the basic programming and data constructs that provide the functionality of the various embodiments of the invention. For example, a database and modules implementing the functionality of the methods described herein may be stored in storage subsystem 56. These software modules will generally be executed by processor 52. In a distributed processing environment, the software modules may be stored on any of a plurality of computer systems and executed by processors of those computer subsystems. Storage subsystem 56 typically comprises memory subsystem 58 and file storage subsystem 60.

Memory subsystem 58 typically includes a number of memories including a main random access memory (RAM) 70 for storage of instructions and data during program execution, and a read only memory (ROM) 72 in which fixed instructions are stored. File storage subsystem 60 may provide persistent (non-volatile) storage for program and data files, and may include tangible storage media 29 (see FIG. 1) which may optionally embody wavefront sensor data, wavefront gradients, a wavefront elevation map, a treatment map, and/or an ablation table, as well as machine readable code or programming instructions for implementing the data processing and control methods described herein. File storage subsystem 60 may include a hard disk drive, a floppy disk drive (along with associated removable media), a compact digital read only memory (CD-ROM) drive, an optical drive, DVD, CD-R, CD-RW, solid-state removable memory, and/or other removable media cartridges or disks. One or more of the drives may be located at remote locations or on other connected computers at other sites coupled to computer system 22. The modules implementing the functionality of the present invention may be stored by file storage subsystem 60.

Bus subsystem 54 provides a mechanism for letting the various components and subsystems of computer system 22 communicate with each other as intended. Although a single bus subsystem is shown schematically, alternate embodiments the bus may utilize multiple bus systems.

Computer system 22 can be of various types including a personal computer, a portable computer, a work station, a computer terminal, a network computer, a control system in a wavefront measurement system or laser surgical system, a mainframe, or another appropriate data processing system.

As computers and networks change over time, the description of computer system 22 shown in FIG. 2 represents only an example for purposes of illustration of an embodiment of the invention, and many other configurations of computer systems are possible.

As noted above, laser system 100 may correct both regular and irregular optical errors of the eye. Regular optical errors (such as spherical errors associated with myopia and hyperopia, and cylindrical errors associated with standard cylindrical stigmatism) can be measured using any of a wide variety of commercially available diagnostic devices, including phoropters, automated refractometers, trial lenses, and the like. While a variety of devices and systems have also been developed and to measure irregular optical errors of the eye (including topographers, tomography systems, and the like) any irregular astigmatism or high-order aberrations of the eye will often be measured using a wavefront system.

Figure 3:
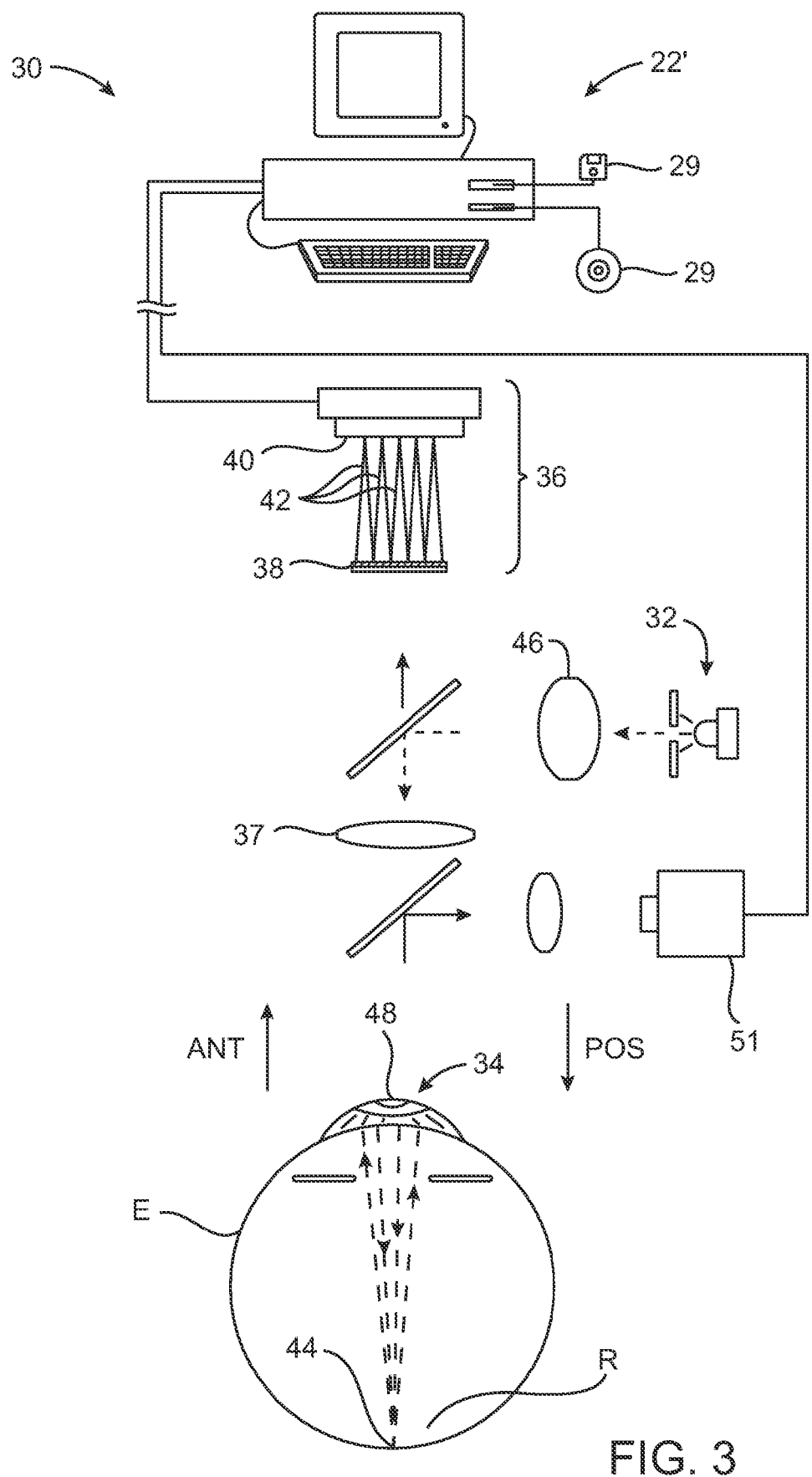
FIG. 3 schematically illustrates a wavefront measurement system for measuring the regular and/or irregular refractive errors of the eye for use with the surgical systems of FIGS. 1 and 1A.

Referring now to FIG. 3, one embodiment of a wavefront measurement system 30 is schematically illustrated in simplified form. In very general terms, wavefront measurement system 30 is configured to sense local slopes of a wavefront exiting the patient's eye. Devices based on the Hartmann-Shack principle generally include a lenslet array to sample the slopes across the pupil of the eye. Thereafter, the local slopes are analyzed so as to reconstruct the wavefront surface or map, often using Zernike polynomial expansion methods.

More specifically, one wavefront measurement system 30 includes a light source 32, such as a laser, which projects a source image through refractive tissues 34 of eye E so as to form an image 44 upon a surface of retina R. The image from retina R is transmitted by the refractive system of the eye (e.g., refractive tissues 34) and imaged onto a wavefront sensor 36 by system optics 37. The wavefront sensor 36 communicates signals to a computer system 22' for measurement of the optical errors in the optical tissues 34 and/or determination of an optical tissue ablation treatment program. Computer 22' may include the same or similar hardware as the computer system 22 illustrated in FIGS. 1 and 2. Computer system 22' may be in communication with computer system 22 that directs the laser surgery system 10, or some or all of the computer system components of the wavefront measurement system 30 and laser surgery system 10 may be combined or separate. If desired, data from wavefront sensor 36 may be transmitted to a laser computer system 22 via tangible media 29, via an I/O port, via a networking connection 66 such as an intranet or the Internet, or the like.

Wavefront sensor 36 generally comprises a lenslet array 38 and an image sensor 40. The reflected light from retina R is transmitted through optical tissues 34 and imaged onto a surface of image sensor 40 and the eye pupil P is similarly imaged onto a surface of lenslet array 38. The lenslet array separates the transmitted light beam into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Light source 32 generally sends light in a posterior orientation through optical tissues 34 onto retina R as indicated in FIG. 3. Optical tissues 34 again transmits light reflected from the retina anteriorly toward wavefront sensor 36. Image 44 actually formed on retina R may be distorted by any imperfections in the eye's optical system when the image source is originally transmitted by optical tissues 34. Optionally, image projection optics 46 may be configured or adapted to decrease any distortion of image 44.

In some embodiments, projection optics 46 may decrease lower order optical errors by compensating for spherical and/or cylindrical errors of optical tissues 34. Higher order optical errors of the optical tissues may also be compensated through the use of an adaptive optics system, such as a deformable mirror. Use of a light source 32 selected to define a point or small spot at image 44 upon retina R may facilitate the analysis of the data provided by wavefront sensor 36. Regardless of the particular light source structure, it will be generally be beneficial to have a well-defined and accurately formed image 44 on retina R.

The wavefront data may be stored in computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 (FIG. 3) image. Such information may include the available information on the wavefront error of the eye and is typically sufficient to reconstruct the wavefront or a desired portion of it. In such embodiments, there may be no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While embodiments of the invention will generally be described with reference to sensing of an image 44, it should be understood that a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

Figure 4:
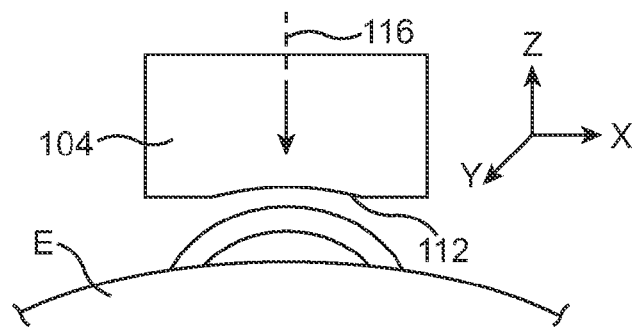
FIG. 4 is a schematic side view of a simplified model of an eye and tissue-shaping surface and body for use in the system of FIG. 1.
Figure 5:
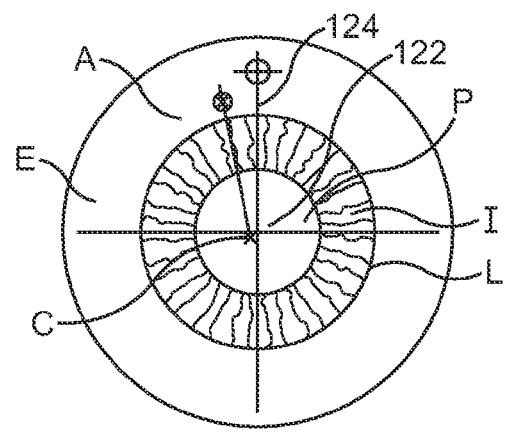
FIG. 5 is a schematic illustration of an image taken from along the optical path through the image shaping body of FIG. 4, showing horizontal and rotational alignment offsets between the tissue shaping body and tissues of the eye, as maybe identified using image processing software in the system of FIG. 1.

Referring now to FIG. 4, treatment of eye E often begins by aligning body 104 with the eye. Body 104 will often be moved horizontally (in the X-Y plain) so as to align an optical axis 116 of the laser treatment system and tissue-shaping surface 112 with the corneal tissues. The eye may be imaged through body 104 as schematically illustrated in FIG. 5, and known image processing techniques can be used to identify a position and orientation of the eye with reference to a pupil P, features of the iris I, an outer edge of the iris or limbus L, or the like. Body 104 and/or eye E may be moved horizontally so as to align a center C of pupil P with a center 122 of surface 112. Additionally, body 104 may be rotated about axis 116 so as to align an stigmatism axis A of eye E with a cylindrical axis 124 of surface 112.

Positioning of the eye E relative to body 104 may be determined using a variety of methods and systems for tracking torsional orientation and position of an eye, including those described in U.S. patent application Ser. No. 10/300,714, filed by the assignee of the present application on Nov. 19, 2002, now published as U.S. Patent Publication No. US2003/0223037 A1), the full disclosure for which is incorporated herein by reference. Such tracking techniques often make use of the striations in the iris I and the location of the pupil boundary for torsional and horizontal positioning, respectively. This information may be provided to the various motion stages of support system 106 (see FIG. 1) to drive body 104 into alignment with the eye. Alternatively, the eye may be aligned with the axis 116 by relying, in at least some dimensions, upon fixation of the eye on a viewing target, with engagement between the tissue-shaping surface 112 into the eye occurring only when the alignment is within an acceptable range, such as when any alignment offsets are less than or equal to desired thresholds.

As will be described in more detail below, absolute alignment between positioning surface 112 and the tissue of the eye need not be provided. So long as the alignment is within an acceptable range, some adjustment of the effective location of the imposed refractive shape may be provided by adjusting the laser target surface. If the engagement between the tissue-shaping surface 112 and eye is sufficiently inaccurate that offsets (either horizontally, between pupil center C and surface center 122, or torsionally between astigmatism axis A and cylinder axis 124) exceeds a desired threshold, then the body 104 may be disengaged from the eye, the eye or the body repositioned, and the body again being advanced into engagement with the eye. This may continue until the alignment offsets are within the desired thresholds. The thresholds may be established so as to allow sufficient adjustment to the final refractive correction using changes to the laser target surface, so that the depth range of the laser target surface may effect the acceptable alignment offsets. Calculation of the laser target surface, and changes to the laser target surface so as to accommodate alignment offsets, may be implemented using any of a wide range of optical analytical tools that have been developed and commercialized, including those used for customized wavefront-based laser eye surgery and the like.

Figure 6:
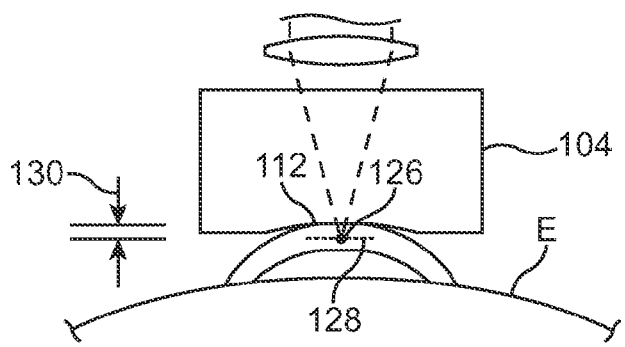
FIG. 6 is a schematic side view showing engagement between the tissue-shaping surface and cornea, and also shows a tissue incision depth range.
Figure 7:
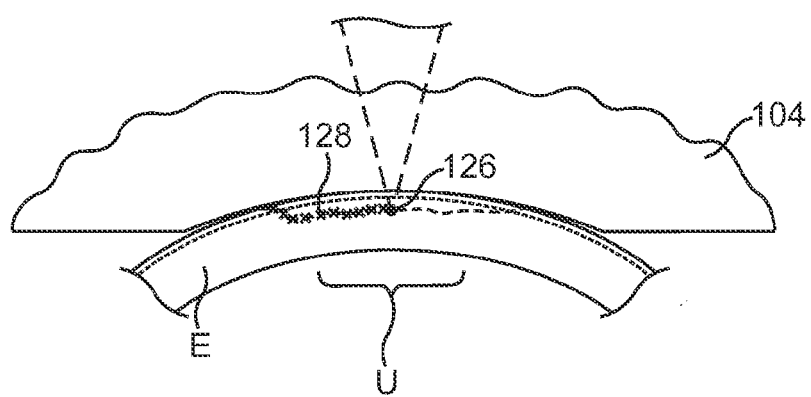
FIG. 7 is a detailed side view of the tissue-engaging surface and corneal tissue conforming thereto from FIG. 6, and shows laser incision of the corneal tissue along a target tissue surface within a limited depth range, such that both the regular and irregular refractive errors of the eye ere mitigated.

Referring now to FIG. 6, once body 104 and the eye E are sufficiently aligned, the body is pressed against the corneal tissues of the eye so that the corneal tissues can form to the shape of surface 112. As can be understood with reference to FIGS. 6 and 7, the cornea need not conform to surface 112 throughout the entire tissue-shaping surface and/or cornea, so long as the cornea conforms to the desired shape throughout an optically used portion U of the corneal tissues of eye E. While the cornea conforms to surface 112, the laser energy from the laser 102 (See FIG. 1) is focused at a spot 126, and the spot is scanned along a target laser surface 128 within the cornea.

Structures and methods for focusing and scanning the laser spot within the cornea so as to incise the corneal tissue are described in a variety of references, including U.S. Pat. Nos. 6,325,792 and 6,899,707, the patents and patent applications assigned to Intralase Corporation of Irvine Calif., and the like. Laser systems and devices for forming incisions in the cornea using focused laser energy (often for use in LASIK procedures) may be commercially available from Intralase and others. Known corneal laser incision techniques often incise the cornea along a plane, often while the corneal surface is applanated so as to form a thin epithelial flap of relatively constant thickness. Embodiments of the present invention will often vary the target laser surface from such a plane (or other standard surface shape, such as a sphere or the like). Nonetheless, such embodiments will often limit a range of depth 130 of the target laser surface 128 as measured from a plane (or other surface). By conforming the corneal tissue to a standard refractive shape such as by use of tissue-shaping surface 112, and by incising the cornea along a plane, a standard refractive correction of the cornea could be effected. By instead varying the depth of the target surface 128 from a nominal plane (or other shape) per any alignment offsets between the surface 112 and the eye, and per any desired high-order alternations of the eye (such as those that may be implemented for alleviation of presbyopia, the irregular refractive errors of the eye, or the like), a wide variety of refractive improvements may be made to the eye.

Figure 7A:
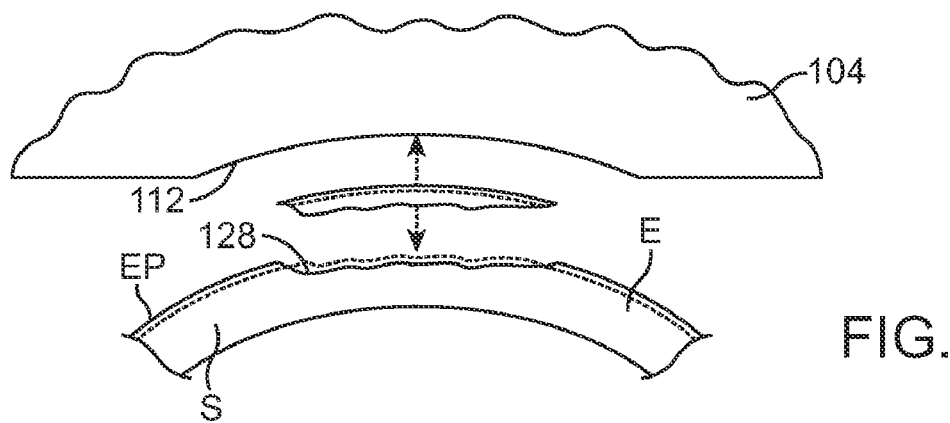
FIG. 7A is a schematic side illustration of the tissue-shaping surface and corneal tissue after the incision of the FIG. 7 is complete, and after the tissue between the target tissue surface and tissue-shaping body has been removed.

Referring now to FIG. 7A, the corneal tissues of the eye E generally include an epithelial layer EP disposed over stroma S. After the laser has incised the stroma and epithelial layer along target laser surface 128, body 104 may be retracted proximally from engagement with the eye, so that the anterior tissue (including both epithelium and stroma) bordered by the laser target surface 128 may be mechanically removed from the eye. The tissue may be removed by grasping the tissue with micro forceps, displacing the tissue using a flow of fluid (either liquid or gas), grasping the tissue using a vacuum applied through a port in surface 112 or a hand-held implement, or the like. Where the laser target surface 128 has been determined based on the high-order for refractive errors of the eye, and where the general curvature of the remaining incised tissue surface reflects the curvature of tissue-shaping surface 112, removal of this anterior tissue can effect both high-order or irregular refractive correction and low-order or regular refractive correction of eye E. Appropriate tissue removal shapes may be determined using ray tracing or wavefront analysis, through empirical studies, and the like, and will often reflect the anticipated epithelial regrowth from the incision formed along the target laser surface. The incision need not be complete when body 104 is retracted, as small remaining contact points can optionally be separated by pulling of the severed tissue body. Techniques developed to facilitate formation of a LASIK flap, including the formation of ablation reservoirs, applanation lens support and vacuum tissue affixation systems, alternating locations along the target surface to inhibit thermal damage, and the like, may be modified for use in laser incising of the corneal tissues along the target surface.

Figure 8:
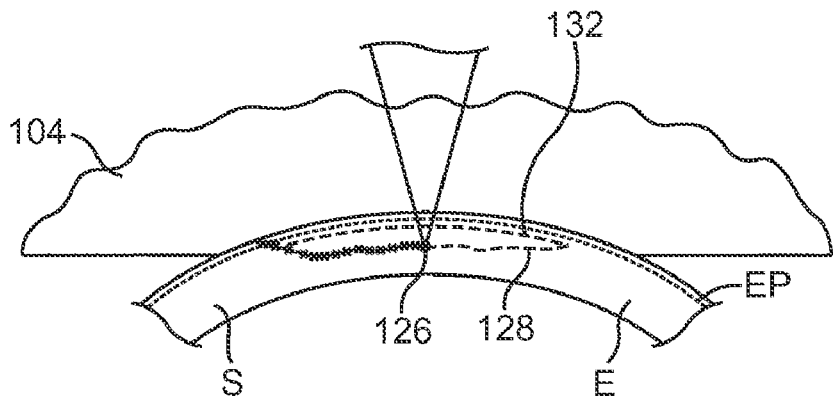
FIG. 8 schematically illustrates an alternative system and method in which two tissue surfaces are incised by the laser.
Figure 8A:
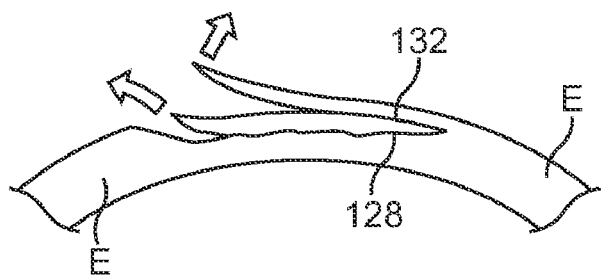
FIGS. 8A and 8B schematically illustrates displacement of an epithelial flap, removal of tissue between the target tissue surfaces, and replacement of the flap with effective refractive correction for both regular and irregular refractive errors.
Figure 8B:
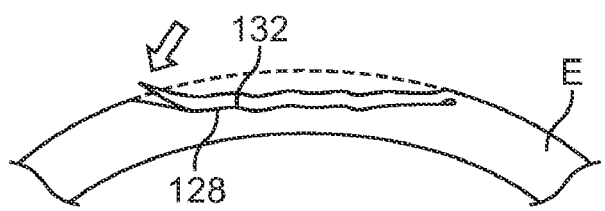

Referring now to FIGS. 8, 8A, and 8B, an alternative embodiment makes use of two separated laser target surfaces and temporary deflection of an epithelial flap so as to minimize delays for epithelial regrowth and the like. As illustrated in FIG. 8, a first laser target surface 128 is determined based on the high-order aberrations of the eye and/or the like. Laser spot 126 is scanned along first target surface 128, with incising of the tissue of the eye limited along one edge of the laser target surface. A second laser target surface 132 is determined, for example, at a fixed distance from tissue-shaping surface 112, or from a flat planar surface similar to those used for formation of a standard LASIK flap. As illustrated in FIGS. 8A and B, again similar to standard LASIK, the flap may be temporarily displaced, allowing the corneal tissues between the first and second laser target surfaces 128, 132 to be mechanically removed. The flap may then be laid back over the modified cornea, so that the tissues bordered by the laser target surfaces 128 and 132 engage and attach to each other. Once again, the final corneal surface will reflect both the regular refractive correction associated with tissue-shaping surface 112 and the high-order aberration corrections of target laser surface 128, but without here having to wait for epithelial regrowth to enjoy the benefits of the procedure.

Figure 8C:
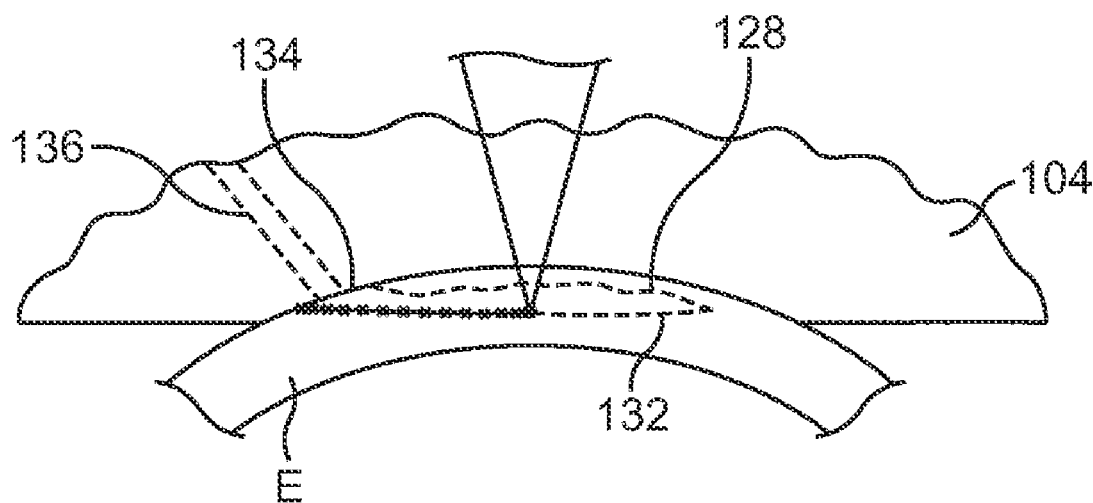
FIG. 8C illustrates embodiments of methods and systems related to those of FIG. 8A, with the irregular refractive error being compensated for using the anterior laser target surface and the posterior laser target surface being planer.
Figure 8D:
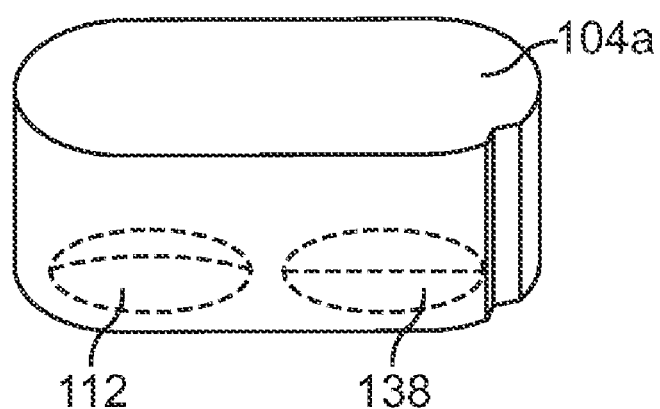
FIG. 8D illustrates an alternative tissue-shaping body having a plurality of tissue-shaping surfaces.

As illustrated in FIG. 8C, alternative embodiments are also possible, such as by forming a planer posterior incision and a target laser 128 reflecting the high order aberrations of the eye at an interior position. The tissue targeted for removal may extend to an exposed tissue region 134 engaged by body 104, and a vacuum port 136 of the body may be used to displace the flap and remove the tissue bordered by the incisions when body 104 is withdrawn proximally away from eye E. Additional ports in body 104 (or an adjacent structure of system 100) may provide fluid or gas flow to help separate the corneal tissues from the tissue-shaping surfaces and the like, to apply a vacuum to affix the engaged eye relative to the delivery optics, and the like. As illustrated in FIG. 8D, alternative tissue-shaping bodies 104A may include multiple tissue-shaping surfaces, such as a first tissue-shaping surface 112 corresponding to a standard refractive error, and a planar tissue-shaping surface 138 for formation of a uniform-thickness tissue flap during scanning along second laser target surface 132. Switching between the tissue-shaping surfaces may be implemented using the motion stages of support structure 106. Still further alternatives are available, including applying any residual or high-order alterations on both the posterior and anterior target laser surfaces, which may increase the total adjustment power available for a given intrastromal depth adjustment range.

Figure 9:
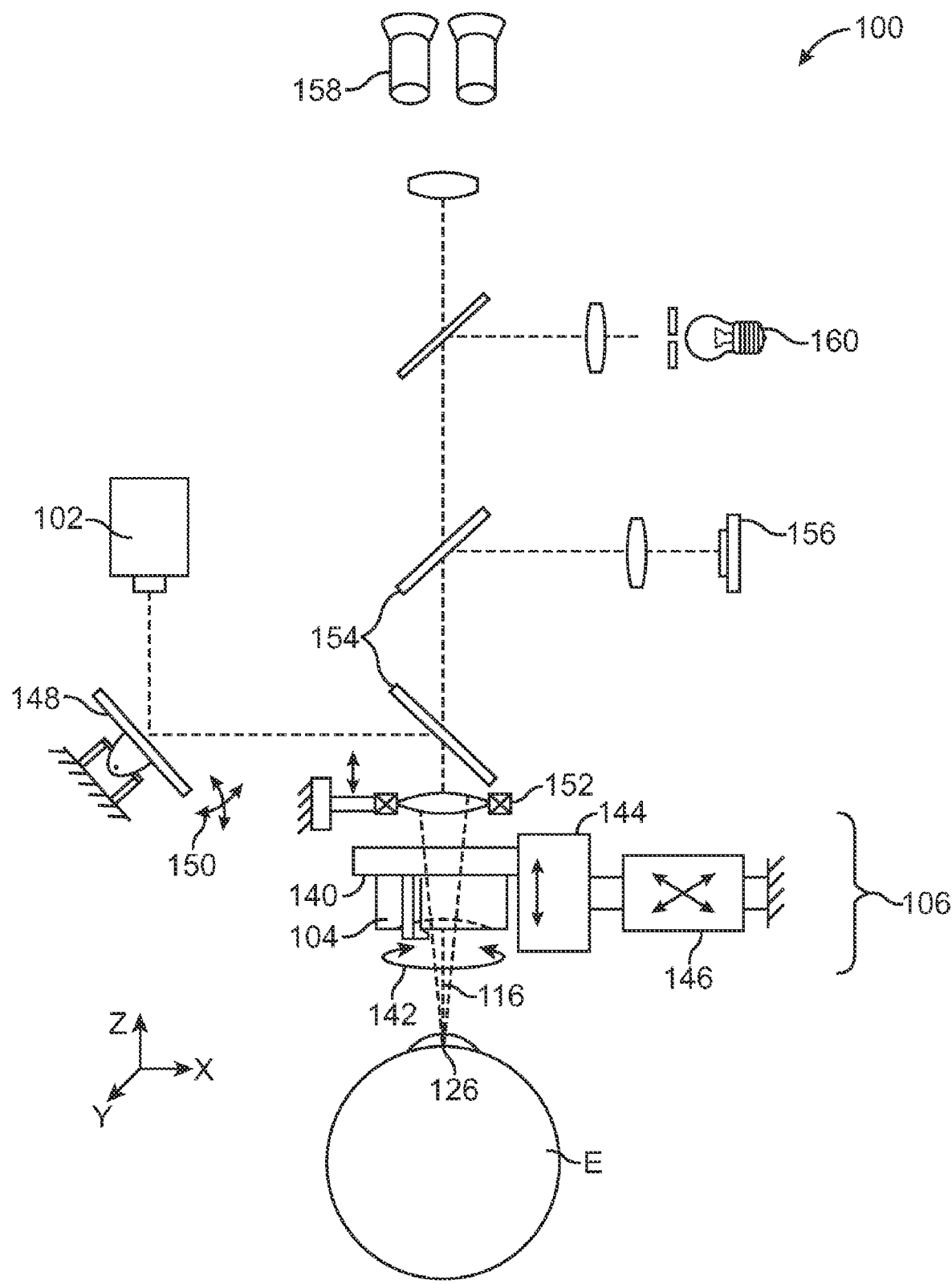
FIG. 9 schematically illustrates some of the optical and structural components of the laser system of FIG. 1.

Referring now to FIG. 9, some of the optical and support system components are schematically illustrated. Shaping body 104 is mounted in a receptacle 140 having a rotational drive for rotating the shaping body about the axis 116, as indicated by arrows 142. Translation of shaping body 104 along axis 116 so as to engage the shaping body against eye E is provided by a Z axis translation/engagement motion stage 144, while horizontal positioning of the shaping body in the X-Y plain is effected using a two dimensional X-Y translation stage 146. In some embodiments, one or more of these motions may be manually effected, such as by having the system user pre-position body 104 at an orientation appropriate for the patient's astigmatism axis.

To effect lateral scanning of the laser energy from laser 102, a two dimensional scanning mirror 148 optionally pivots in two dimensions, as indicated by arrows 150. Alternative arrangements may employ a first scanning mirror to scan the laser energy along the X axis, and a second scanning mirror having a pivot axis angularly offset from that of the first mirror may provide scanning primarily along the Y axis. Still further alternative scanning mechanisms may be employed, including X-Y translation of an offset imaging lens, and the like. Scanning of the laser spot 126 along axis 116 may be effected by movement of one or more focusing lens 152 along the optical path in between the laser and eye. As the scanning rate of the laser spot 126 within the tissue of the eye E may be quite rapid, it will generally be beneficial to minimize the weight of any electro mechanical scanning elements, drive the scanning elements with relatively high speed actuators such as galvanometers, and the like.

Many of the remaining optical and control components of system 100 may be similar to (or modified from) components of existing laser eye surgery systems. For example, the optical path may employ a series of beam splitters 154 to selectively direct portions of the light from eye E, optionally using wavelength-selective reflection. An image sensor 156 may capture an image of the eye through shaping body 104 and other components along the optical path, with the captured image often being used for establishing and/or verifying alignment between the eye and shaping body 104, laser spot 126, and other components of the optical path. Signals from the image sensor 156 may be used to identify a center of the pupil of eye E, a rotational orientation of eye E, and the like. Such signals may be used to drive the various motion stages of support structure 106 and movable optical components of optics 108 per calculations of processor 22 (See FIG. 1). Images from image sensor 156 may also be used to measure alignments offsets and the like as described above. Images may also be displayed on a display screen of the laser eye surgery system, which may be used in conjunction with (or instead of) direct viewing of the procedure through binocular microscope 158. Additional optical and/or mechanical components of system 100 may also be included, including a fixation target 160, additional lenses and groups of lenses for processing the light on the optical path, and the like.

Figure 10A:
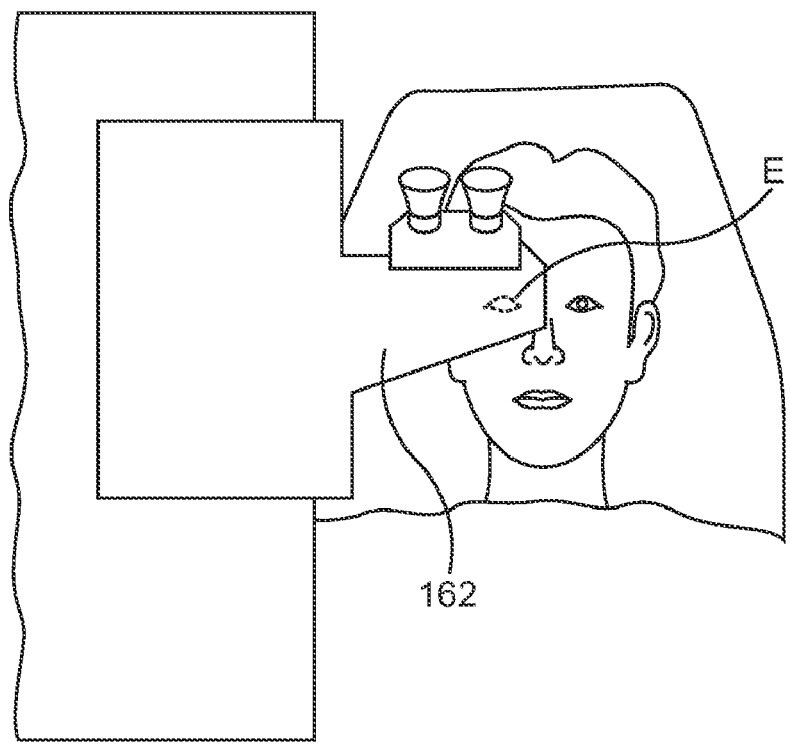
FIGS. 10A and 10B are top and side views, respectively, of a laser delivery arm of the system of FIG. 1.
Figure 10B:
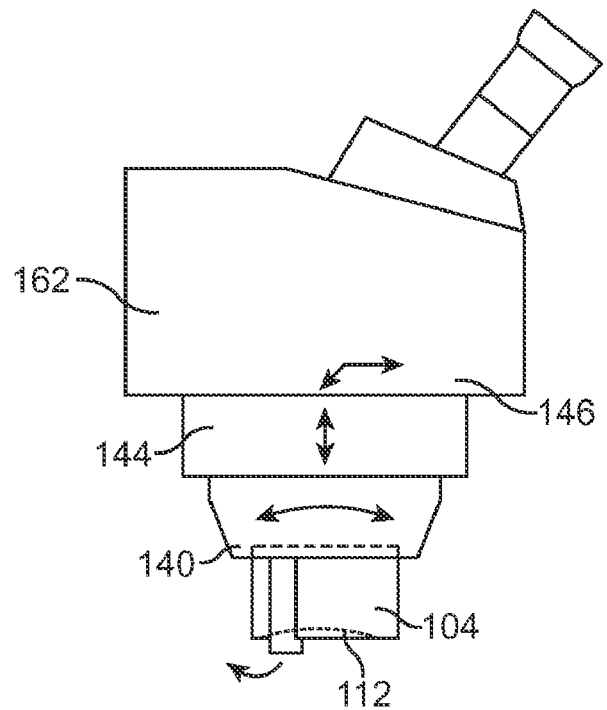

Referring now to FIGS. 10A and 10B, top and side views, respectively, of a support arm 162 show many of the components described above regarding support system 106. The rotational stage of receptacle 140, the axial translation stage 144, and the horizontal motion stage 146 may be arranged in a variety of differing orders, or may be combined or separated into fewer or more individual stages having different degrees of freedom in a wide variety of possible arrangements. The receptacle 140 will preferably receive shaping body 104 and engage positioning surfaces of the shaping body so as to allow accurate positioning and rotation of the shape and body into alignment with the eye. While a simple latch of the receptacle is schematically illustrated, no structure of the receptacle will typically extend beyond the shaping body so as to interfere with engagement between the shaping surface 112 and the eye E.

Figure 11:
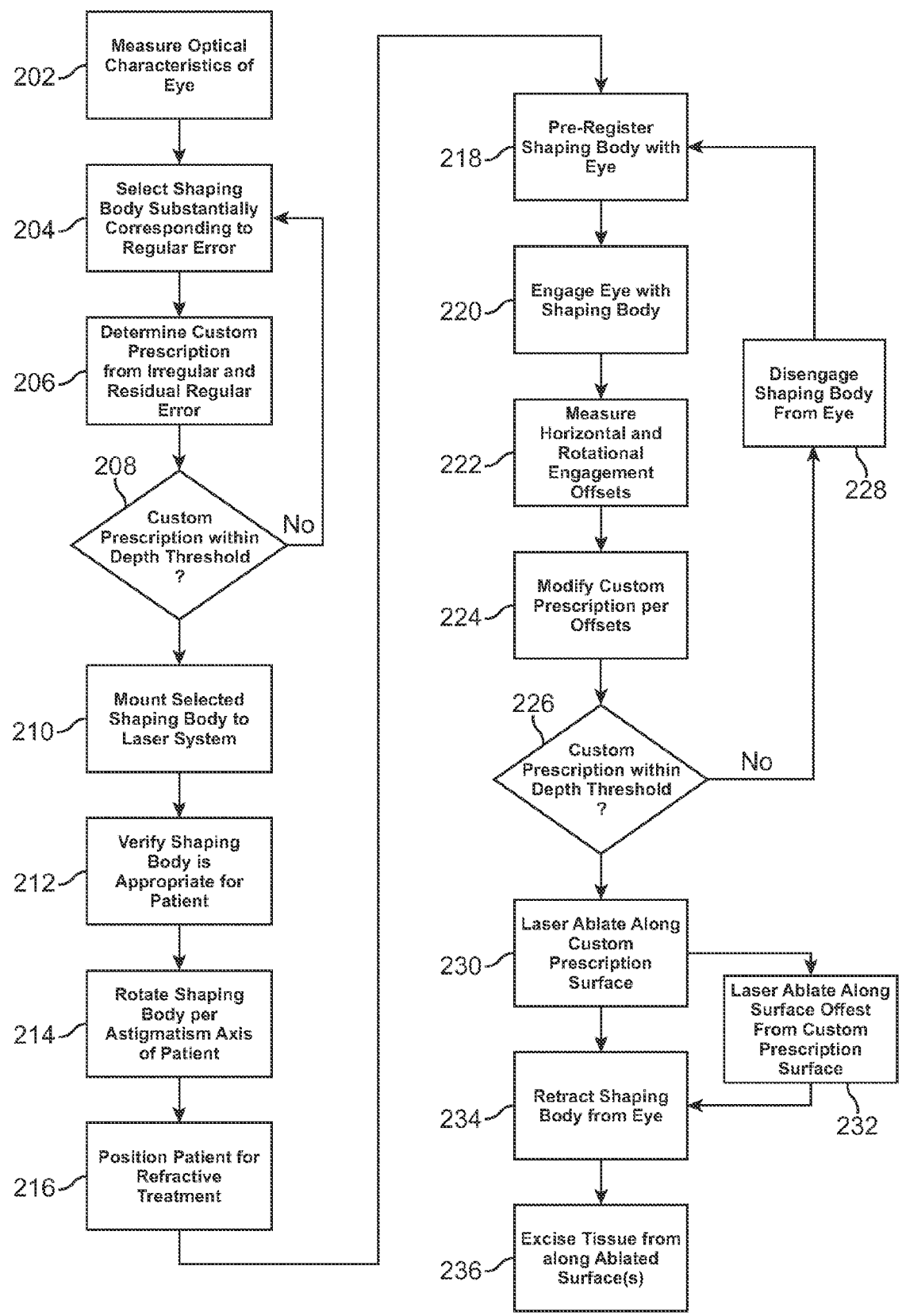
FIG. 11 is a flow chart schematically illustrating a method for treating an eye so as to correct regular and irregular refractive errors.

Referring now to FIG. 11, a method 200 may be used to correct regular refractive errors of the eye and impose desired irregular refractive alterations, such as correcting high order aberrations of the eye, impose multifocal shapes on the eye suitable for mitigating presbyopia, and the like. Method 200 will often begin with measurement of the optical characteristics of the eye 202, with exemplary measurements comprising wavefront measurements and/or otherwise providing information on both regular and irregular refractive errors of the eye. A shaping body will be selected 204 having a tissue-shaping surface that substantially corresponds to a regular error of the eye.

Substantially corresponding shapes may have shapes which correspond exactly to the refractive error of the eye, or which are the closest corresponding spherical and/or cylindrical powers available within a given set of alternatively selectable tissue-shaping surfaces. In many embodiments, particularly those in which additional high-order adjustments to the eye prescription will be made, the substantially corresponding body may not be the single closest corresponding shape, but will often be among the subset of shaping bodies having powers which are the nearest more positive spherical and/or cylindrical power, the nearest more negative spherical and/or cylindrical power, or the like. Hence, where a set of shaping bodies has uniform one diopter increments in both cylindrical and spherical power, an eye having 2.2 diopters of the sphere and 3.3 diopters of cylinder may be treated by selecting a shaping body having spherical, cylindrical powers of: (2, 3), (3, 3), (2,4), or (3, 4). In some embodiments, particularly when high levels of irregular refractive alterations will be imposed and/or when the set of alternatively selectable shaping bodies has small increments in power, the set may include a shaping body which has a power that is between that of the regular refractive error of the eye and that of the selected substantially corresponding shaping body. Such circumstances may be the exception, and the substantially corresponding shaping body will typically be closer to the measured standard refractive error of the eye than most of the non-selected shaping bodies of the set, and often closer than at least 75% of the shaping bodies of the set.

Based on the measured optical characteristics of the eye 202 and the selected shaping body 204, a custom laser target surface shape or prescription 206 will be determined. As described above, the custom prescription may be determined from the irregular refractive shape, and/or from any residual regular error that would otherwise remain if the tissue-shaping surface power alone or used. Hence, in our example of an eye having 2.2 D of spherical error and 3.3 D of cylindrical error, assuming a 2 D sphere/3 D cylinder body is selected, the target laser surface will be adjusted so as to provide an additional 0.2 D of sphere and 0.3 D of cylinder. Any additional refractive changes, such as multifocal shapes to mitigate presbyopia (such as those more fully described in U.S. patent application Ser. No. 10/738,358, filed on Dec. 5, 2003, and entitled "Presbyopia Correction Using Patient Data", the full disclosure of which is incorporated herein by reference) may also be included. The target laser surface can then be compared with any depth range or threshold 208. If the target laser surface has variations in depth which exceed the capabilities of the laser system or a safe range for the cornea of that particular patient, an alternative shaping body may be selected, and/or some modification of the proposed custom laser target surface may be calculated so as to provide a viable prescription.

Once the shaping body and custom prescription are identified, the shaping body is mounted to the laser system 210. The system may verify that the shaping body is appropriate for the patient 212, often by a transmission of signals between the processor 22 of system 100 and a signal source 98 of shaping body 104 (See FIG. 1). The signal source 98 may comprise a memory chip, a radio frequency identification (RFID) structure or tag of body 104, or the like. The signals transmitted from the signal source 98 may comprise or indicate the power of the tissue-shaping surface 112 of the mounted body 104, and may also identify that particular mounted body. The processor can use these signals to verify that the mounted body has the appropriate power for the corrected custom prescription of the eye, and may also verify that the particular body mounted on the system has not already been used in a prior procedure so as to present dangers to the patient due to degradation in the optical qualities of the shaping body, sterilization issues, and the like. The transmitted signals may also be used to verify that the shaping body is suitable for use on the laser system on which it is mounted (avoiding incompatibility issues), to verify regulatory approval of the combination of the mounting body and system for use in treating the patient, to verify that the system user (as entered into the system via an input device) has appropriate training for the procedure, and/or to allow the manufacturer and/or a regulatory body to monitor use of that particular laser treatment system. By controlling distribution of bodies 104 having appropriate signal sources, the manufacture may also collected fees from the user of the system 100, with monitoring and/or fee collection often being performed via a network coupled to processor 22. If processor 22 determines the shaping body is not appropriate for use in the procedure for any reason, the processor may, in response, inhibit or prevent the procedure from going forward and the eye from being treated with that shaping body.

Once the shaping body has been verified, the shaping body will be rotated so as to align the cylindrical axis (if any) of tissue-shaping surface 112 on the cylindrical body with an astigmatism access of the eye. The patient will be positioned for treatment 216, and the shaping body preregistered with the eye 216 (often using an image of the eye taken through the shaping body as described above). The order of the axial rotation of the shaping body, positioning of the patient, and preregistration of the shaping body with the eye 218 may be altered as appropriate, and at least some of these alignment steps may be implemented manually. For example, the patient and/or chair may be manually positioned by the physician, the eye may be aligned at least in part by having the patient view a fixation target, and/or the shaping body (optionally with its receptacle) may be manually rotated into alignment with patient's astigmatism axis.

When the shaping body and the eye appear to be the appropriately preregistered, the tissue-shaping surface and the shaping body are advanced into engagement with the eye 220 so as to conform the tissues of the cornea with the shape of the tissue-shaping surface. Horizontal and/or rotational engagement offsets are measured, typically by imaging the eye through body 104 and using image processing techniques such as those that have been developed for tracking of the eye during known laser eye surgery procedures. Measured offsets 222 may be used to modify the custom prescription, for example, so as to compensate for rotational offsets between the cylindrical power axis of the shaping body and the astigmatism axis of the eye, so as to laterally offset the cylindrical power and/or spherical power, or the like. Known optical shape calculation methods may be employed for such modification of the custom prescription 224, and the custom prescription may again be checked against depth thresholds 226 of the laser system and/or patient cornea. If the engagement offsets are excessive and/or the custom prescription depths now exceeds the allowable range, the shaping body may be disengaged 228, with re-registration and re-engagement hopefully providing an acceptable custom shape.

As described above regarding claims 7 and 7A, laser incising on the custom prescription 230 may be used to sever a desire to shape from the anterior corneal surface, so that epithelial regrowth provides the desired enhanced refractive characteristics. Alternatively, as described with reference to FIGS. 8A through C, a second laser incision 232 may be implemented, with tissue removed from between the two incisions so as to retain the existing epithelial layer of the cornea. It should be noted that the incisions need not absolutely sever the tissues from the eye, as any relatively small remaining connection points may be detached by mechanical excision, such as by simply pulling the substantially severed tissues.

After ablation along the target laser the surface or surfaces is complete, shaping body 104 may be retracted 234 away from the eye E and the desired tissue excised from along the one or more target laser surfaces 236.

While the exemplary embodiments have been described in some detail, by way of example and for clarity of understanding, a variety of modifications, changes, and adaptations will be obvious to those of skill in the art. Hence, the scope of the present invention is limited solely by the appended claims.

What is claimed is:

1. A method for altering refraction of an eye, the eye having a regular refractive error and capable of benefiting from desired irregular refractive alteration, the method comprising:

selecting a tissue-shaping surface from among a set of alternative shaping bodies having tissue-shaping surfaces corresponding to differing regular refractive errors, the selected tissue-shaping surface substantially corresponding to the regular refractive error;

engaging the selected tissue-shaping surface against the eye so as to conform the eye to the selected tissue-shaping surface;

determining a three-dimensional laser target surface in response to the desired irregular refractive alteration of the eye; and scanning a laser spot in three-dimensions through tissue of the engaged eye along the laser target surface so as to mitigate the regular error and effect the desired irregular refractive alteration of the eye.

2. The method of claim 1, wherein the set of alternative shaping bodies define a series of spherical and cylindrical steps in power therebetween, wherein the selected tissue-shaping surface corresponds with a selected power, the selected power differing from the regular error of the eye by a power difference, the power difference being less than an associated step in power of the shaping bodies, and wherein the laser target surface is also determined so as to compensate for the power difference.

3. The method of claim 2, wherein the steps in power are each less than or equal to two times a maximum power adjustment of the laser target surface.

4. The method of claim 2, wherein the steps in power are less than or equal to 3.0 diopters.

5. The method of claim 2, further comprising adjusting the laser target surface per a desired presbyopia-mitigation shape.

6. The method of claim 1, wherein each of the set of alternative selectable tissue-shaping surfaces is disposed on a shaping body comprises a laser transmissive material having laser delivery alignment surfaces and a signal source, the signal source configured to generate signals indicative of an associated power and an identifier of that particular body, and further comprising verifying mounting of an appropriate body for the eye and inhibiting re-use of each of the alternative selectable bodies using the signals.

7. The method of claim 1, wherein the regular error of the eye comprises a cylindrical error having an astigmatism axis, and further comprising rotating the tissue-shaping surface into alignment with an astigmatism axis of the eye.

8. The method of claim 1, further comprising checking alignment between the tissue-shaping surface and the eye after engaging the tissue-shaping surface against the eye.

9. The method of claim 8, wherein the alignment is checked by capturing an image of the engaged eye and determining a horizontal offset and cyclotorsional offset between the engaged eye and the tissue-shaping surface, and further comprising, in response to one or both of the offsets exceeding an alignment threshold, displacing the tissue-reshaping surface away from the eye, moving the eye or the tissue-shaping surface to correct alignment, and re-engaging the tissue-shaping surface against the eye.

10. The method of claim 8, further comprising adjusting a location of the target laser surface relative to the tissue-shaping surface and a shape of the target laser surface in response to an alignment offset between the tissue shaping surface and the eye.

11. The method of claim 1, further comprising mechanically excising tissue from between the target laser surface and the tissue-shaping surface so that the eye has enhanced refractive characteristics after re-growth of removed epithelial tissue.

12. The method of claim 1, further comprising scanning the laser spot along another laser target surface so that first and second tissue surfaces are defined by the laser target surfaces, and mechanically excising tissue from between the first and second tissue surfaces so that the eye has enhanced refractive characteristics when the first tissue surface engages the second tissue surface.

13. The method of claim 1, wherein the laser spot comprises a femtosecond laser spot and separates the tissue of the eye along the laser target surface in about 30 seconds or less, and wherein separated tissue bordered by the laser target surface is primarily mechanically removed rather than primarily relying on volumetric photoablative resculpting.

14. A method for customized correction of an eye, the method comprising:
measuring a regular refractive error and an irregular refractive error of the eye, the regular refractive error comprising a spherical error and a cylindrical error, the cylindrical error having a cylindrical power and an astigmatism axis;
selecting a tissue-shaping body in response to the regular refractive error of the eye from among a set of alternative tissue-shaping bodies having differing associated spherical and cylindrical powers, the selected tissue-shaping body having a selected tissue-shaping surface, a spherical power substantially corresponding to the spherical error of the eye, and a cylindrical power substantially corresponding to the cylindrical error of the eye;
aligning a cylindrical axis of the selected tissue-shaping body with the astigmatism axis of the eye;
engaging the, selected tissue-shaping surface against the eye so as to conform an eye surface to the selected tissue-shaping surface;
determining a three-dimensional target laser surface in response to the irregular refractive error of the eye;
incising tissue of the eye by scanning a laser spot in three dimensions through the tissue along the laser target surface; and
mechanically excising tissue bordered by the laser target surface so as mitigate the regular refractive error and the irregular refractive error of the eye.

15. The method of claim 14, wherein the target laser surface differs from a nominal surface shape by less than a depth threshold, the depth threshold corresponding to a power of about 1.5 diopters or less.

16. A system for altering refraction of an eye, the eye having a regular refractive error and is capable of benefiting from a desired irregular refractive alteration, the system comprising:
a set of alternative tissue-shaping bodies having tissue-shaping surfaces and differing regular refractive powers;
a tissue incising laser for transmitting a laser beam along an optical path;
a support for positioning a selected tissue-shaping body along the optical path, the selected tissue-shaping body selected from among the set;
a processor for determining a three-dimensional laser target surface in response to the desired irregular refractive alteration of the eye; and
beam scanning optics coupled to the processor for scanning the beam in three dimensions along the laser target surface to incise tissue from the eye when the eye engages and conforms to the selected tissue-shaping surface such that removal of the incised tissue mitigates the regular errors of the eye and effects the desired irregular alteration.

17. The system of claim 16, wherein the set of alternative shaping bodies define a series of spherical and cylindrical steps in power therebetween.

18. The system of claim 17, wherein the steps in power are each less than or equal to two times a maximum power adjustment of the laser target surface.

19. The system of claim 17, wherein the steps in power are less than or equal to 3.0 diopters.

20. The system of claim 17, wherein the selected tissue-shaping surface corresponds with a selected power, the selected power differing from the regular error of the eye by a power difference, the power difference being less than an associated step in power of the shaping bodies, and wherein the processor is configured to determine the target laser surface so as to compensate for the power difference.

21. The system of claim 16, wherein the processor is configured to adjust the laser target surface per a desired presbyopia-mitigation shape.

22. The system of claim 16, wherein each of the set of alternative selectable tissue-shaping surfaces is disposed on an associated shaping body, the shaping bodies comprising a material transmissive to the laser beam and having laser delivery alignment surfaces and a signal source, the signal source configured to generate signals indicative of the selected power and an identifier of that particular body, the signals suitable for inhibiting re-use of the alternative selectable bodies.

23. The system of claim 16, wherein the regular error of the eye comprises a cylindrical error having an astigmatism axis, and wherein the support rotatably supports the tissue-shaping surface about the optical path for alignment of the tissue-shaping surface with the astigmatism axis of the eye.

24. The system of claim 16, further comprising an image capture device optically coupled to the optical path for imaging the eye when the eye engages the tissue-shaping surface, the processor coupled to the image capture device and configured to determine alignment between the tissue-shaping surface and the eye after engaging the tissue-shaping surface against the eye.

25. The system of claim 24, wherein the processor is configured to determine a horizontal offset and cyclotorsional offset between the engaged eye and the tissue-shaping surface in response to alignment data from the image capture device, and wherein the support further comprises a displacement stage coupled to the processor for displacing the tissue-reshaping surface away from the eye and re-engaging the tissue engagement surface against the eye in response to one or both of the offsets exceeding an alignment threshold.

26. The system of claim 25, wherein the processor is further configured for adjusting a location of the target laser surface relative to the tissue-shaping surface and a shape of the target laser surface in response to an alignment offset between the tissue shaping surface and the eye.

27. The system of claim 16, wherein the processor is configured to scan the laser spot along another laser target surface so that first and second tissue surfaces are defined by the laser target surfaces, and such that mechanically excising tissue from between the first and second tissue surfaces and engaging the first tissue surface with the second tissue surface enhances refractive characteristics of the eye.

28. The system of claim 16, wherein the laser comprises a femtosecond laser and the processor is configured to separates the tissue of the eye along the laser target surface in about 30 seconds or less.

29. A tissue-shaping body for use with a system for altering refraction of an eye, the eye having a regular refractive error and an irregular refractive error, the system including a support for positioning the body along an optical path from a laser, and beam scanning optics for scanning in three-dimensions along a three-dimensional laser target surface to incise tissue of the eye when the eye engages the body such that removal along the incised tissue mitigates the regular and irregular errors of the eye, the body comprising:
 a material transmissive of light from the laser; and
 a tissue-shaping surface defined by the material, the tissue-shaping surface having a cylindrical power substantially corresponding to the regular refractive error of the eye.

30. The body of claim 29, further comprising a signal source for transmitting a signal, the signal indicative of the cylindrical power and an identifier of the particular body suitable for inhibiting re-use of the body.

31. The body of claim 30, further comprising a set of alternatively selectable tissue-shaping bodies having differing tissue-shaping surfaces corresponding to differing cylindrical and spherical refractive powers.

* * * * *